United States Patent [19]
Starchevich

[11] Patent Number: 6,015,119
[45] Date of Patent: Jan. 18, 2000

[54] COMBINATION HOLDING AND STABILIZING DEVICE

[76] Inventor: Jovanka Starchevich, 138 Sullivan St., New York, N.Y. 10012

[21] Appl. No.: 09/197,048

[22] Filed: Nov. 20, 1998

Related U.S. Application Data

[60] Provisional application No. 60/105,860, Oct. 27, 1998.

[51] Int. Cl.[7] ........................................ F16L 3/08
[52] U.S. Cl. ........................ 248/65; 128/DIG. 6; 604/180
[58] Field of Search .................... 248/65, 74.3, 205.2; 604/180; 128/DIG. 6

[56] References Cited

U.S. PATENT DOCUMENTS

| | | | |
|---|---|---|---|
| 3,630,195 | 12/1971 | Santomieri | 128/DIG. 6 X |
| 3,834,380 | 9/1974 | Boyd | 128/DIG. 6 X |
| 4,706,914 | 11/1987 | Ground | 248/74.3 |
| 5,389,082 | 2/1995 | Baugues et al. | 604/180 X |
| 5,390,883 | 2/1995 | Songhurst | 248/74.3 X |
| 5,709,665 | 1/1998 | Vergano et al. | 604/180 X |
| 5,810,781 | 9/1998 | Bierman | 604/180 X |
| 5,827,230 | 10/1998 | Bierman | 604/180 X |

*Primary Examiner*—Ramon O. Ramirez
*Attorney, Agent, or Firm*—Howard C. Miskin

[57] ABSTRACT

A combination holding and stabilizing device for cylindrical objects comprises a combination of two components, a securing unit and an anchoring unit. The securing unit has an elongated longitudinal body having a top surface with adhesive and first and second lateral portions extending from a fold line. The second lateral portion foldably overlaps the first lateral portion for holding and stabilizing a cylindrical object therebetween. At both ends of the body, the top surface of the first and second portions have separable holding elements to releasably secure the first and second portions together to allow quick and easy adjustment of the cylindrical object. The anchoring unit has an elongated longitudinal body having a bottom surface with adhesive. The anchoring unit is longer than the first lateral portion of the securing unit such that the bottom surface of the securing unit is attached to the top surface of the anchoring unit with the anchoring unit extending beyond at least the axis of the fold line. In an alternate embodiment, embedded longitudinally in the body of the securing unit is at least one thin plastic strip. The plastic strip is malleable and conforms to the shape of the cylindrical object to increase the holding and stabilizing power of the securing unit.

16 Claims, 4 Drawing Sheets

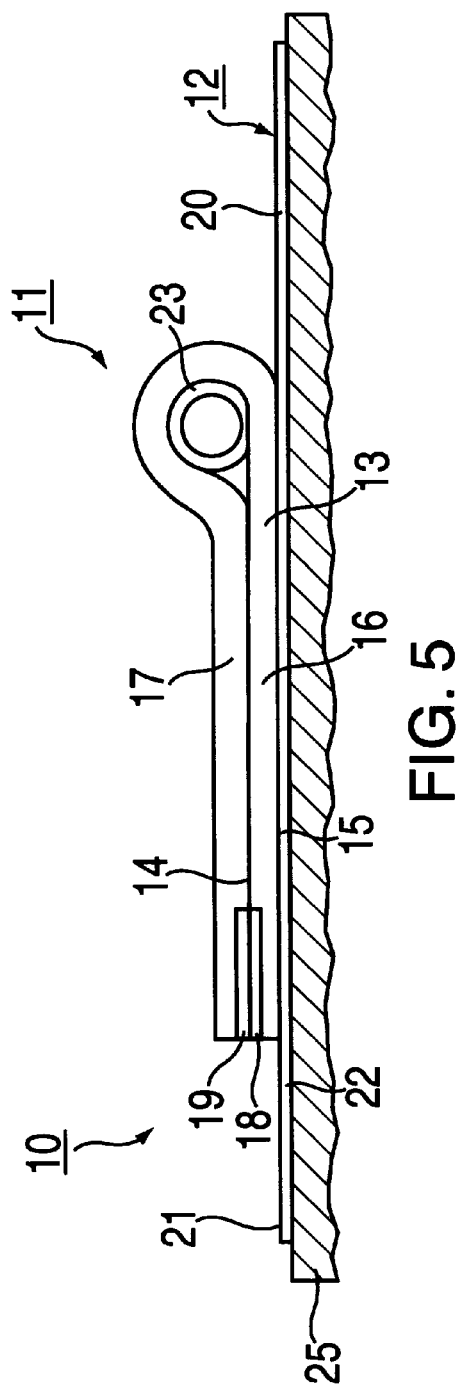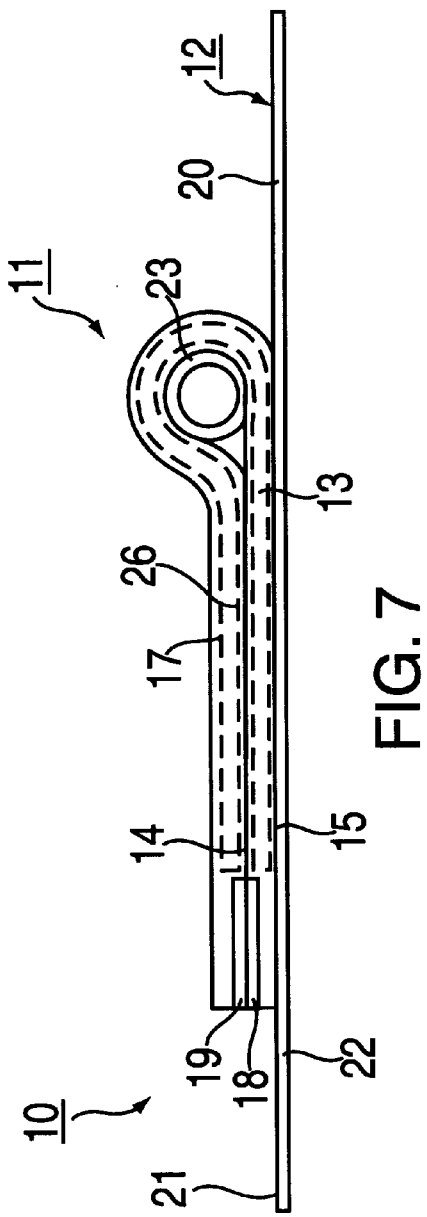

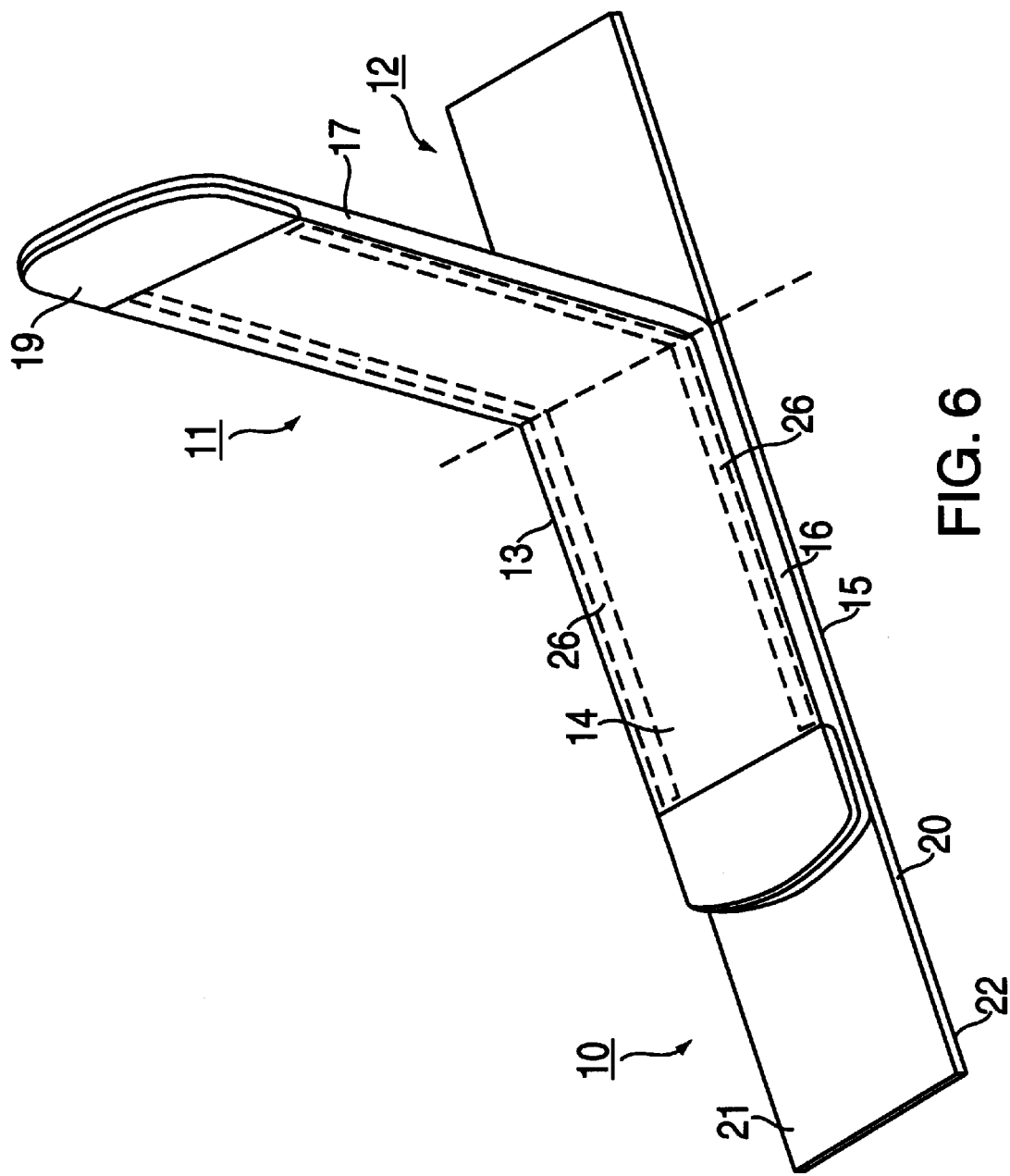

COMBINATION HOLDING AND STABILIZING DEVICE

This application claims the benefit of U.S. Provisional Application Ser. No. 60/105,860, filed Oct. 27, 1998.

FIELD OF THE INVENTION

The invention relates to a device for securely retaining and stabilizing tubular, cylindrical or similar objects. In particular, a combination holder and stabilizer for securing medical tubes, rods and/or catheters applied to a patient.

BACKGROUND OF THE INVENTION

In the medical field, cylinders, tubes and catheters are routinely used to interface different parts of a patient's body, such as for infusion and drainage therapies. For example, intravenous (I.V.) treatment, Foley catheters, nasal gastric treatment, etc. Infusion and drainage therapies are often cumbersome and uncomfortable to the patient as it require the connection and support of tubes and/or catheters to the patient. Discomfort to a patient increases if the tube and/or catheter is not securely attached to the patient in an accurate position. In many instances, the positioning, stability and secured retainment of the tubes and/or catheters is crucial to the outcome of the treatment, and certainly to the comfort of the patient on which it is used.

An insecurely retained tube and/or catheter can lead to many complications and cause discomfort to the patient, such as accidentally withdrawal from the patient's body, which disrupts the treatment. Even in cases where the insecurely retained tube and/or catheter is not completely removed from the body, needless interference with the positioning of the tube and/or catheter can cause problems to the patient. For example, unexpected, inadvertent movement of an I.V. tube can cause the needle to damage the wall of the vein or blood vessel. For nasal gastric treatment, constant accurate positioning of the tube in the nostril and through the nasal passage is critical. An improperly positioned tube can cause the tube to either adhere to the stomach walls and cause the stomach lining to bleed or cause erosion through the nasal septum and, in extreme cases create a hole in the nasal septum.

The traditional method of securing tubes and/or catheters to a patient is the use of adhesive tapes such as surgical tape or bandage. Adhesive tapes cannot securely retain tubes and/or catheters for accurate positioning due to the thinness and pliability of the tapes. The tube and/or catheters may be accidentally twisted or removed from the patient. Secure retainment is compromised if the adhesive power of non-surgical grade tape is traded off for breathability of the skin of surgical tape for minimal irritation. Stability of the tube and/or catheter is further compromised by having the tube and/or catheter rests directly against the flexible, compressible and movable skin of a patient.

During the course of an infusion or drainage treatment, which can last for several weeks to several months, it is often necessary to adjust the positioning of the tube and/or catheter during use. The traditional use of adhesive tape to secure a tube and/or catheter does not provide an easy method of adjustment of the tube and/or catheter. To adjust these normally requires the removal and replacement of the adhesive tape after repositioning the tube and/or catheter because the adhesive power of the tape decreases substantially from the oily excretions from the patient's skin. Over a period of time, such removal and replacement of the tape causes discomfort to the patient, such as sensitive skin, irritation and pain.

Therefore, there is a need for a device that comfortably, quickly and securely retains and stabilizes tubes and/or catheters applied to a patient yet facilitates easy repositioning and readjustment of the tubes and/or catheters, with little discomfort.

SUMMARY OF THE INVENTION

The invention provides a combination holding and stabilizing device that quickly and securely positions and retains tubes, cylinders, such as catheters to a patient's body yet facilitates repositioning of the tube and/or catheter with a minimum of discomfort to the patient.

The combination holding and stabilizing device of the present invention preferably comprises a combination of two components, a securing unit and an anchoring unit. The securing unit is for holding and stabilizing a cylinder, tube and/or catheter at a constant position relative to the device of the present invention. The anchoring unit is for holding and stabilizing the securing unit at a constant position relative to a fixed location, such as a patient's body. The securing and anchoring units work cooperatively to achieve the optimal retainment, flexibility in choice of placement, and security of tubes and/or catheters to a patient.

The securing unit of the present invention has preferably a generally elongated body such as a rectangular shaped longitudinal body made of a layer of thin flexible foam having a first top surface and a second bottom surface. The body has first and second lateral portions, preferably equal in size, extending from a fold line whereby the second lateral portion foldably overlays the first lateral portion. The top surface of the body has a resealable adhesive for securing a tube and/or catheter sandwiched between the first portion and the second overlay portion along the axis of the folding line for optimal stability. Advantageously, at both ends of the elongated body, the top surface of the first and second portions have separable holding elements such as corresponding hooks and loops of a VELCRO™ interlocking mechanism to both releasably secure the first and second portions together and to facilitate separation of the second overlay portion from the first portion for quick and easy adjustment of the tube and/or catheter.

Illustratively, the anchoring unit of the present invention has a rectangular shaped longitudinal body, similar to the securing unit, having a first top surface and a second bottom surface. The bottom surface has adhesive for attaching to a fixed location. The anchoring unit has a length proportionally longer than the first portion of the securing unit. The bottom surface of the first portion of the securing unit is attached to the top surface of the anchoring unit with the anchoring unit extending beyond at least the axis of the fold line of the securing unit to provide maximum anchoring and stability to the tubes and catheters secured in the securing unit. It is preferable that the anchoring unit is a medical-grade adhesive tape, which is generally known to one skilled in the art, that is suitable for application to a patient's skin.

In an alternative embodiment of the present invention, the foam body of the securing unit has at least one thin plastic strip embedded longitudinally across the body. The plastic strip is malleable and pliable to the extent that when it is pressed against the tube and/or catheter in the securing unit, it molds and conforms to the shape of the tube and/or catheter to increase the holding and stabilizing power of the securing unit. Such plastics having this ability are well-known the art. Another advantage of using plastic strips is the ability to generally decrease the thickness of the foam body without losing the holding and stabilizing power of a thicker and firmer foam.

BRIEF DESCRIPTION OF THE DRAWINGS

These and other features of the invention are delineated in detail in the following description. In the drawings:

FIG. 5 is a front elevational view illustrating the retainment and stability of a tube and/or catheter with the present invention applied to a patient.

FIG. 6 is a perspective view of a second embodiment of the present invention.

FIG. 7 is a front elevational view illustrating the retainment and stability of a tube and/or catheter in a second embodiment of the present invention.

It will be appreciated that, for purposes of illustration, these figures are not necessarily drawn to scale.

DETAILED DESCRIPTION OF THE PREFERRED EMBODIMENTS

Figure 1:
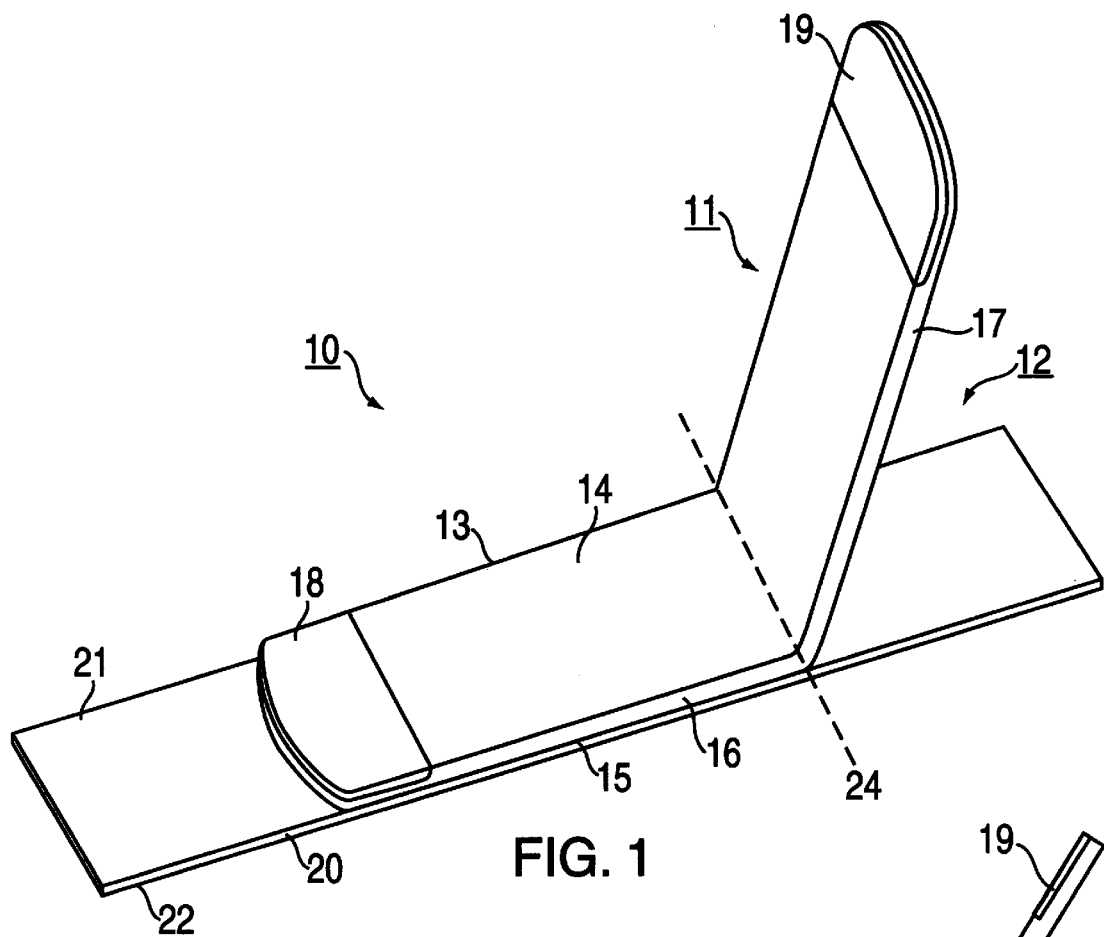
FIG. 1 is a perspective view of the present invention.

With reference to the drawings, wherein the same reference number indicate the same element throughout, there is shown in FIG. 1 a perspective view of the present invention. The present invention, a combination holding and stabilizing device 10 comprises a securing unit 11 atop an anchoring unit 12.

Figure 2:
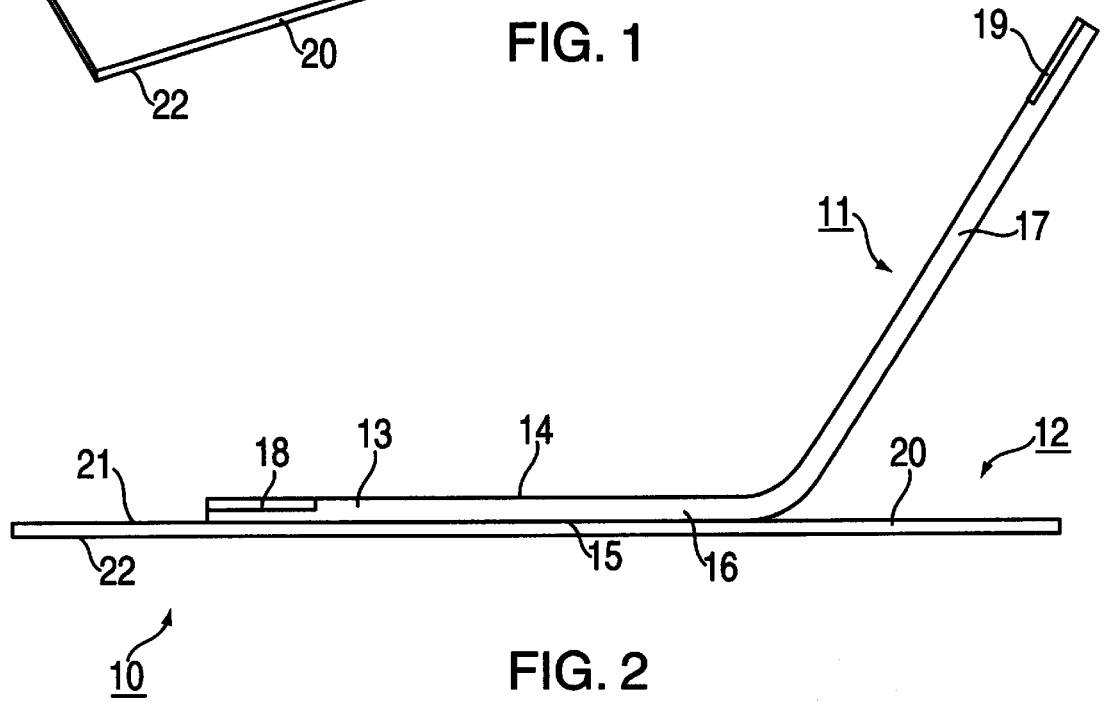
FIG. 2 is a front elevational view of FIG. 1.

As shown in FIGS. 1 and 2, securing unit 11 has a generally rectangular shaped longitudinal body 13 having a top surface 14 and a bottom surface 15. Body 13 has first and second lateral portions 16 and 17, preferably of equal size, whereby the second portion 17 foldably overlays and overlaps the first portion 16. Top surface 14 of body 13 has resealable adhesive for securing a tube and/or catheter placed sandwiched between the first and second portions 16 and 17, as shown in FIG. 5. At each opposite end 18 and 19 of body 13, on the top surface 14, are corresponding hooks and loops, respectively, of a VELCRO™ interlocking mechanism.

Body 13 is preferably made of a layer of thin foam to provide flexibility yet firmness to secure a tube and/or catheter, but other materials know to one skilled in the art, such as pile fabric, may be substituted. Body 13 also serves to absorb moisture and oil excretion from a patient's body. The length of body 13 may vary proportionally to the diameter of the tubes and/or catheters to be secured for maximum secure holding and stability.

The anchoring unit 12 has a generally rectangular shaped longitudinal body 20, similar to body 13 of securing unit 11, having a top surface 21 and a bottom surface 22. The bottom surface 15 of the first portion 16 of securing unit 11 is attached to the top surface 21 of anchoring unit 12 by means known to one skilled in the art, such as gluing, sewing, stapling, VELCRO™ interlocking mechanism, etc. Body 20 of anchoring unit 12 is longer than the first portion 16 of securing unit 11.

Body 20 of anchoring unit 12 is preferably a medical-grade adhesive tape that is suitable for application on a patient skin, such as hydrocolloid adhesive tape that resists breakdown from skin moisture and adhere to skin well but not hair, which is available from, for example, 3M™. The length of body 20 may vary proportionally to the length of the first portion 16 of securing unit 11 for maximum secure holding and stability of the securing unit 11 and the tube and/or catheter attached to securing unit 11.

Figure 3:
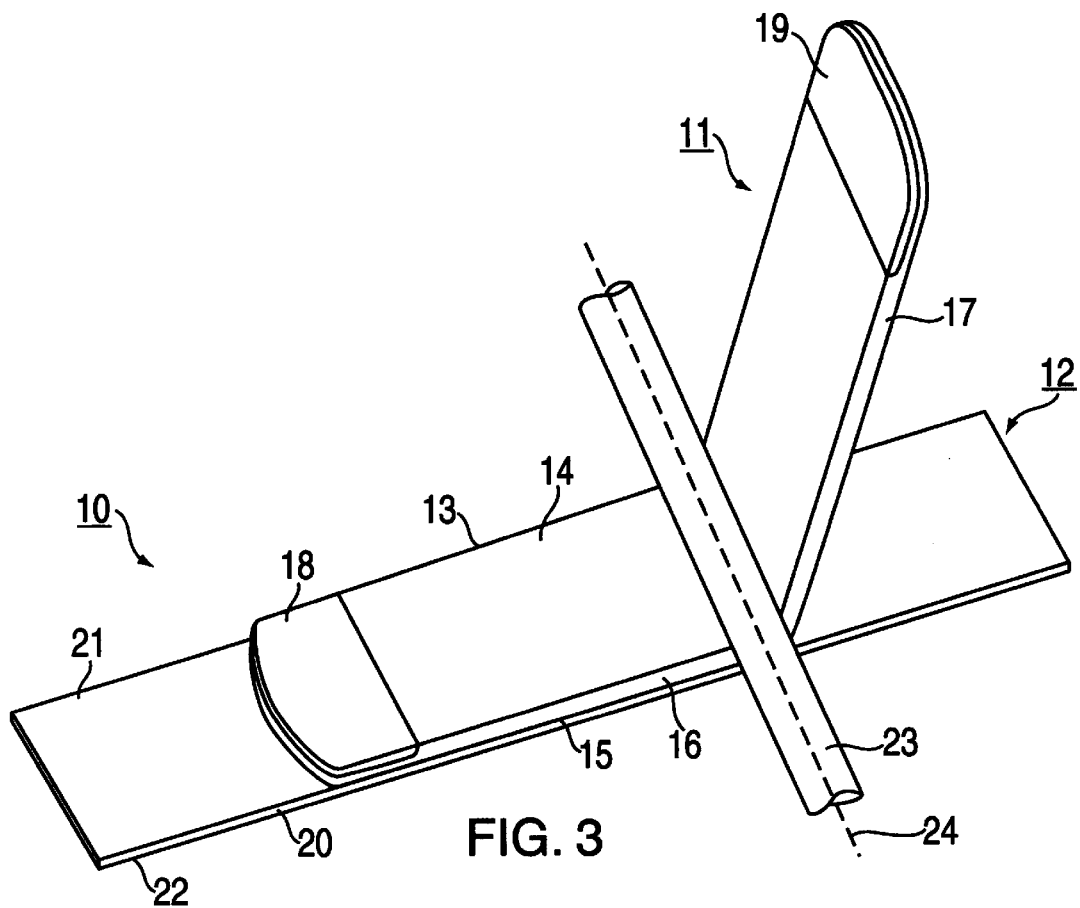
FIG. 3 is a perspective view illustrating the positioning of a tube and/or catheter for maximum retainment and stability.
Figure 4:
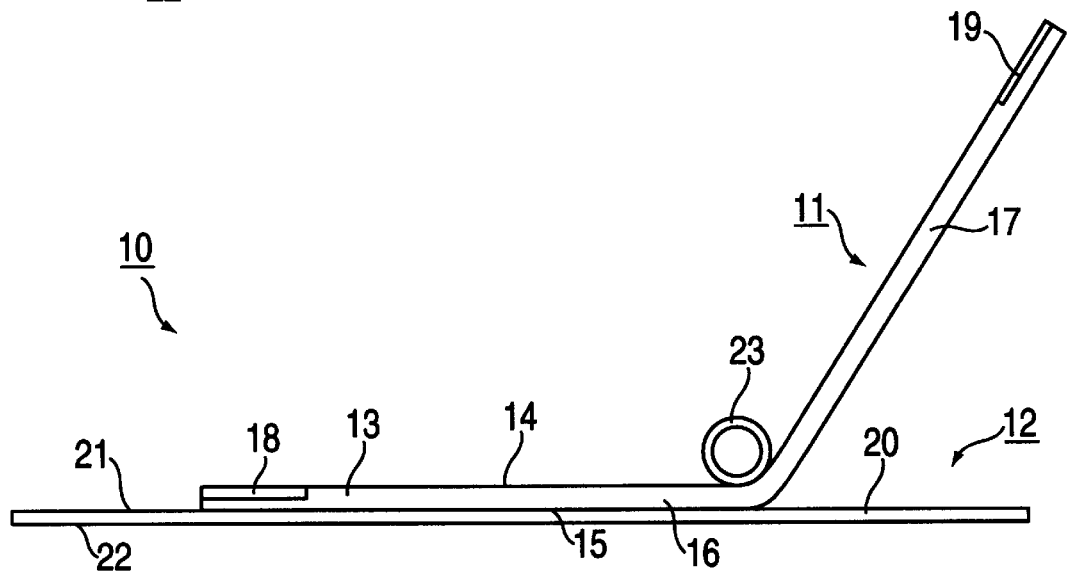
FIG. 4 is a front elevational view of FIG. 3.

The application of the combination holding and stabilizing device 10 is demonstrated with FIGS. 3, 4 and 5. FIGS. 3 and 4 illustrate the positioning of a tube and/or catheter 23 perpendicular to longitudinal body 13 of securing unit 11 along the axis of the fold line 24 where second portion 17 foldably overlays first portion 16 about fold line 24.

As shown in FIG. 5, second portion 17 is folded to overlay first portion 16 of securing unit 11. The resealable adhesive on top surface 14 of securing unit 11 causes first portion 16 to adhere to second portion 17 and sandwiched tube 23 therebetween. Similarly, the hooks and loops at ends 18 and 19, respectively, of securing unit 11 interact to secure the first portion 16 to second portion 17. With tube 23 in alignment with the axis of the fold line 24 and top surface 14 of securing unit 11 adhering to the surface of tube 23, tube 23 is restricted from movement in all directions. The stability of tube 23 is enhanced with the support of foam body 13 of securing unit 11 along the axis of the fold line 24 across the width of body 13.

The anchoring unit 12 in FIG. 5 is applied to a patient's body 25. The adhesive tape of body 20 of anchoring unit 12 is applied to the surface of the patient's skin and can conform to different contour of the body, such as finger, arm, nose and thigh, to be securely attached thereto. As can be seen in FIG. 5, to provide maximum retainment and stability to tube 23 in securing unit 11, anchoring unit 12 extends beyond, at least, the first portion 16 where the second portion 17 folds over the first portion 16.

The removal and adjustment of tube 23 can be easily achieved without disturbing the patient to which the combination holding and stabilizing device 10 is attached. The hooks and loops at ends 18 and 19, respectively, of securing unit 11 can be easily separated to expose top surface 14 of both the first portion 16 and the second portion 17 and tube 23, whereby tube 23 may be re-positioned before again folding second portion 17 over first portion 16 to securely retain tube 23.

An alternate embodiment of the present invention is shown in FIGS. 6 and 7, wherein two plastic strips 26 are embedded longitudinally along body 13 of securing unit 11. The plastic strips 26 are malleable, pliable and capable of conforming to the contour of tube 23 for added secure retainment and stability, as shown in FIG. 7. After positioning tube 23 between first and second portions 16 and 17 of securing unit 11, the plastic strips 26 are molded to act as a skeleton to hold tube 23 in a stable position. The addition of plastic strips 26 allow, generally, the decrease in thickness of foam body 13 of securing unit 11 without compromising the firmness in the holding power of the securing unit 11.

Although certain features of the invention have been illustrated and described herein, other better modifications and changes will occur to those skilled in the art. It is, therefore, to be understood that the appended claims are intended to cover all such modification and changes that fall within the spirit of the invention.

What I claim is:

1. A combination holding and stabilizing device for securely retaining a tubular object at a fixed location comprising:

a securing unit comprises an elongated longitudinal body having a top surface, a bottom surface and first and second opposite ends, said top surface having adhesive for retaining said tubular object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said tubular object placed along said fold line is securely positioned in response to said first and second portions being in superposed position;

an anchoring unit for retaining said device at said fixed location; and means for attaching said securing unit onto said anchoring unit.

2. The device according to claim 1 wherein said securing unit is glued onto said anchoring unit.

3. The device according to claim 1 wherein said securing unit is sewed onto said anchoring unit.

4. The device according to claim 1 wherein said securing unit further comprises at least one plastic strip embedded longitudinally along said body whereby said plastic strip molds and conforms to said tubular object when said second portion foldably overlaps said first portion to retain said tubular object therebetween.

5. The device according to claim 1 wherein said body is made of a layer of thin flexible foam.

6. The device according to claim 1 wherein said body is made of pile fabric.

7. The device according to claim 1 wherein said first and second lateral portions are of equal size.

8. The device according to claim 1 wherein said adhesive on said top surface of said body is resealable adhesive.

9. The device according to claim 1 wherein said anchoring unit comprises an elongated longitudinal body having a top surface and a bottom surface having adhesive for retaining said device at said location.

10. The device according to claim 9 wherein said body is an adhesive tape suitable for application of said device to said fixed location.

11. The device according to claim 9 wherein said body is a medical-grade adhesive tape.

12. The device according to claim 9 wherein said body is a hydrocolloid adhesive tape.

13. A combination holding and stabilizing device for retaining a cylindrical object at a fixed location comprising:

a securing unit comprises:

an elongated longitudinal body having a top surface, a bottom surface, and first and second opposite ends, said top surface having adhesive for retaining said cylindrical object, said body having first and second lateral portions foldable about a fold line to overlie in superposed relation with said corresponding adhesive surfaces facing each other in abutting relation, latching means on said top surface at said first and second ends for holding the respective ends in tight relationship when said second portion foldably overlaps said first portion whereby said cylindrical object placed along said fold line is securely positioned in response to said first and second portions being in superposed position; and at least one plastic strip embedded longitudinally along said body whereby said plastic strip molds and conforms to said cylindrical object when said second portion foldably overlaps said first portion to retain said cylindrical object therebetween;

an anchoring unit comprises an elongated longitudinal body having a top surface and a bottom surface having adhesive for retaining said device at said fixed location; and means for attaching said securing unit to said anchoring unit.

14. The device according to claim 13 wherein said longitudinal body of said anchoring unit is longer than said longitudinal body of said first portion of said securing unit.

15. The device according to claim 14 wherein said anchoring unit extends beyond said fold line of said securing unit.

16. The device according to claim 13 wherein said cylindrical object is a tube.

\* \* \* \* \*